(12) United States Patent
Jones et al.

(10) Patent No.: US 6,650,951 B1
(45) Date of Patent: Nov. 18, 2003

(54) METHOD AND INSULIN PUMP FOR PROVIDING A FORGOTTEN BOLUS WARNING

(75) Inventors: Steven Paul Jones, Rochester, MN (US); Robert Russell Williams, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 472 days.

(21) Appl. No.: 09/596,648

(22) Filed: Jun. 19, 2000

(51) Int. Cl.⁷ .............................................. G06F 17/00
(52) U.S. Cl. ................................ 700/90; 604/65
(58) Field of Search ...................... 700/90; 604/65–67, 604/890.1, 128, DIG. 12, 13

(56) References Cited

U.S. PATENT DOCUMENTS

| | | | |
|---|---|---|---|
| 4,151,845 A | | 5/1979 | Clemens ....................... 604/66 |
| 4,308,866 A | | 1/1982 | Jelliffe et al. .................. 604/31 |
| 4,529,401 A | | 7/1985 | Leslie et al. ................. 604/131 |
| 5,752,235 A | * | 5/1998 | Kehr et al. ...................... 705/3 |
| 5,805,051 A | * | 9/1998 | Herrmann et al. ........ 340/309.4 |
| 5,997,475 A | * | 12/1999 | Bortz .......................... 600/300 |
| 6,167,362 A | * | 12/2000 | Brown et al. .................. 703/11 |
| 6,198,383 B1 | * | 3/2001 | Sekura et al. ............ 340/309.4 |
| 6,379,301 B1 | * | 4/2002 | Worthington et al. ........ 600/309 |
| 6,408,854 B1 | * | 6/2002 | Gonda et al. ................ 128/898 |
| 6,427,088 B1 | * | 7/2002 | Bowman et al. ............... 607/60 |
| 6,485,461 B1 | * | 11/2002 | Mason et al. ................ 604/132 |
| 6,554,798 B1 | * | 4/2003 | Mann et al. ................. 604/131 |

* cited by examiner

*Primary Examiner*—Leo Picard
*Assistant Examiner*—Zoila Cabrera
(74) *Attorney, Agent, or Firm*—Joan Pennington

(57) ABSTRACT

A method and apparatus are provided for providing a forgotten bolus warning for an insulin pump user. User selections for mealtimes are received and stored. A user selection for a warning wait period is received and stored. When a time past a mealtime plus the user selection for the warning wait period is identified, checking for a bolus having been taken is performed. Responsive to no bolus having been taken, the user is alerted with the forgotten bolus warning. The user is alerted with the forgotten bolus warning by an audible, visual, or tactile warning for a programmable period of time. The user selections for mealtimes are received and stored on a daily basis for each day of the week. The user selection for a warning wait period can be received and stored independently for each meal.

16 Claims, 7 Drawing Sheets

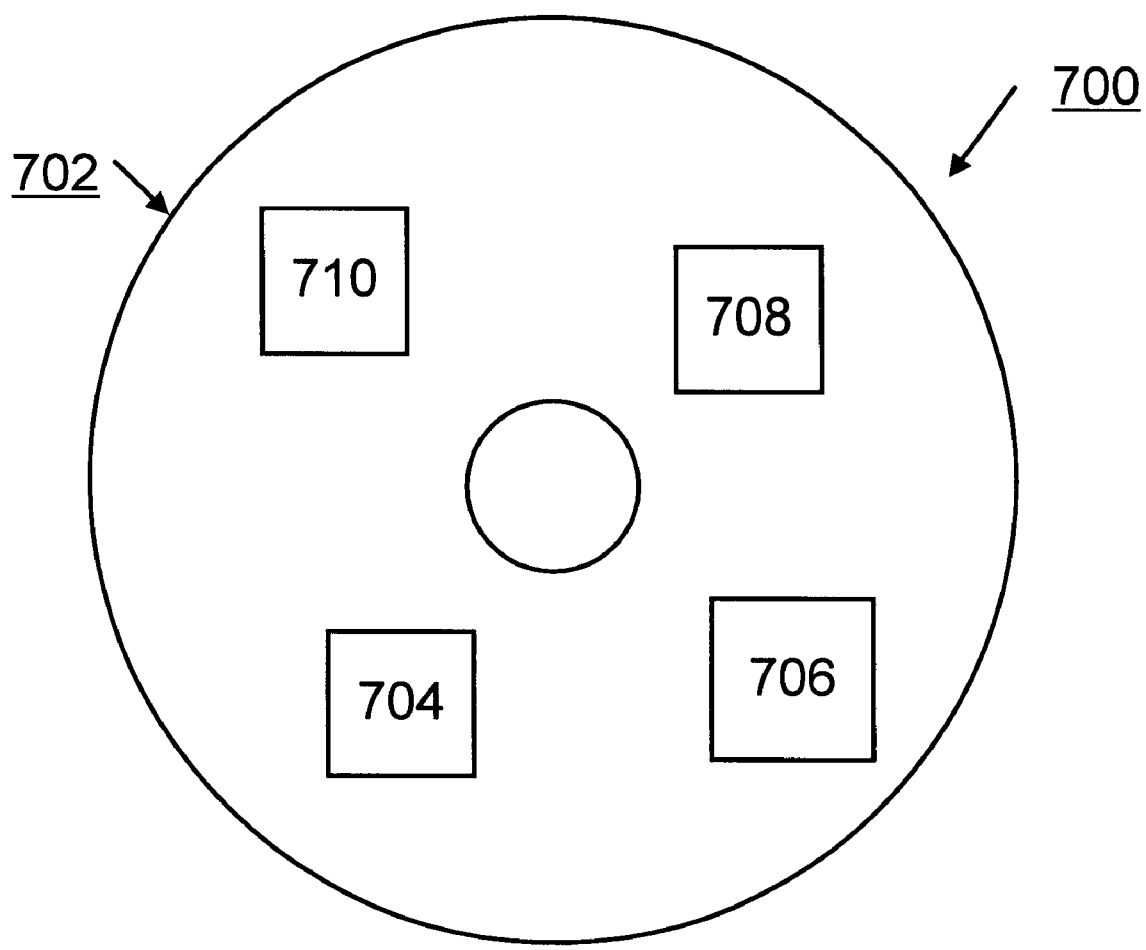

METHOD AND INSULIN PUMP FOR PROVIDING A FORGOTTEN BOLUS WARNING

FIELD OF THE INVENTION

The present invention relates generally to insulin pumps, and more particularly, relates to a method and apparatus for providing a forgotten bolus warning for an insulin pump user.

DESCRIPTION OF THE RELATED ART

Various insulin pumps are commercially available. To achieve the best control of diabetes, many diabetics are turning to use of insulin pumps. An insulin pump is a device that periodically dispenses very small amounts of insulin according to a preprogrammed profile set by the user to cover basal insulin needs. Basal insulin takes care of or covers glucose produced by the body (liver) on a continuous basis. When a diabetic person consumes food, the diabetic person needs to estimate the amount of carbohydrate content in the food and program the pump to administer a bolus amount of insulin to cover the carbohydrates in the meal. For example, if known for a particular individual that one unit of insulin covers 10 grams of carbohydrates, and the meal has 100 grams of carbohydrates, at mealtime the individual would program the pump to administer a bolus amount of 10 units of insulin. Because the bolus amount varies per meal and the diabetic person may skip a meal, an insulin pump is not preprogrammed to administer a bolus amount of insulin.

It is quite easy for a diabetic person to fail to program a bolus at mealtime. The failure to program the bolus can be either a lapse of memory or an error, such as not pushing the pump's button hard enough. If the bolus is not administered, blood sugar levels typically will rise to unhealthy and perhaps dangerous levels. Even if the person feels the high blood sugar effects, by then some harm or risk for diabetic complications have occurred. Usually a diabetic does not sense high blood glucose until it is above 400 mg/dl, whereas the usual target range is 70 mg/dl to 120 mg/dl. While one could take more frequent blood sugar readings with available blood testing equipment, such testing is expensive and painful.

A need exists for a mechanism for providing a forgotten bolus warning for an insulin pump user.

SUMMARY OF THE INVENTION

A principal object of the present invention is to provide a method and apparatus for providing a forgotten bolus warning for an insulin pump user. Other important objects of the present invention are to provide such method and apparatus for providing a forgotten bolus warning for an insulin pump user substantially without negative effect and that overcome many of the disadvantages of prior art arrangements.

In brief, a method and apparatus are provided for providing a forgotten bolus warning for an insulin pump user. User selections for mealtimes are received and stored. A user selection for a warning wait period is received and stored. When a time past a mealtime plus the user selection for the warning wait period is identified, checking for a bolus having been taken is performed. Responsive to no bolus having been taken, the user is alerted with the forgotten bolus warning.

In accordance with features of the invention, the user is alerted with the forgotten bolus warning by an audible, visual, or tactile warning for a programmable period of time. The user selections for mealtimes are received and stored on a daily basis for each day of the week. The user selection for a warning wait period can be received and stored independently for each meal.

BRIEF DESCRIPTION OF THE DRAWINGS

The present invention together with the above and other objects and advantages may best be understood from the following detailed description of the preferred embodiments of the invention illustrated in the drawings, wherein:

FIG. 7 is a block diagram illustrating a computer program product in accordance with the preferred embodiment.

DETAILED DESCRIPTION OF THE PREFERRED EMBODIMENTS

Figure 1:
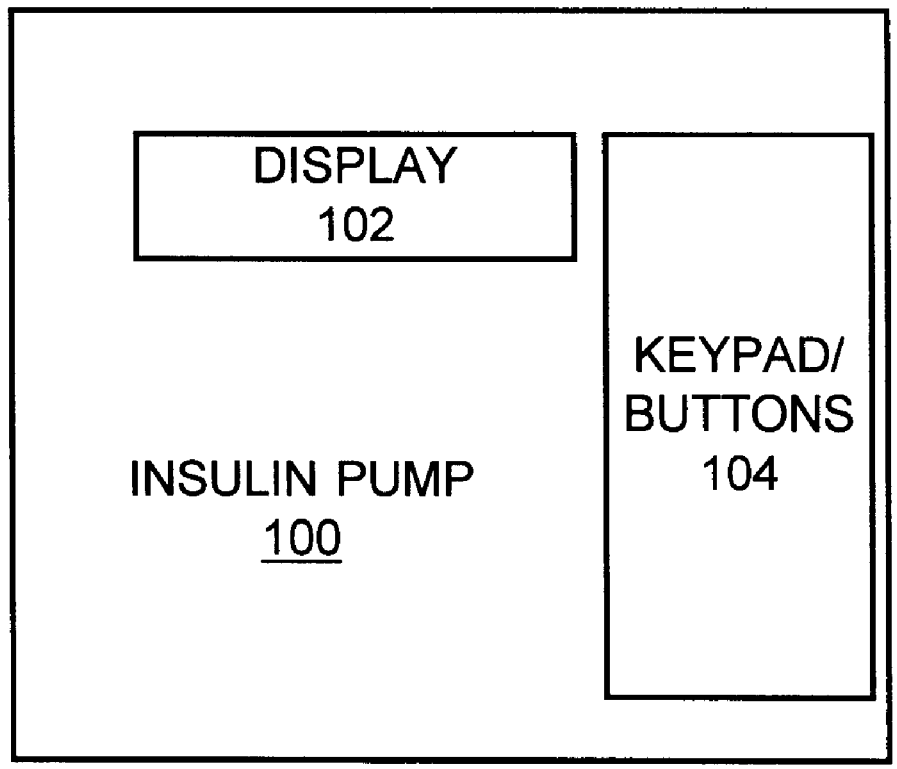
FIG. 1 is a diagram illustrating an exemplary insulin pump in accordance with the preferred embodiment.

Having reference now to the drawings, in FIG. 1, there is shown an exemplary insulin pump of the preferred embodiment generally designated by the reference character 100. As shown in FIG. 1, insulin pump 100 includes a display 102 for viewing by a user and a keypad 104 for receiving user entries.

Figure 2:
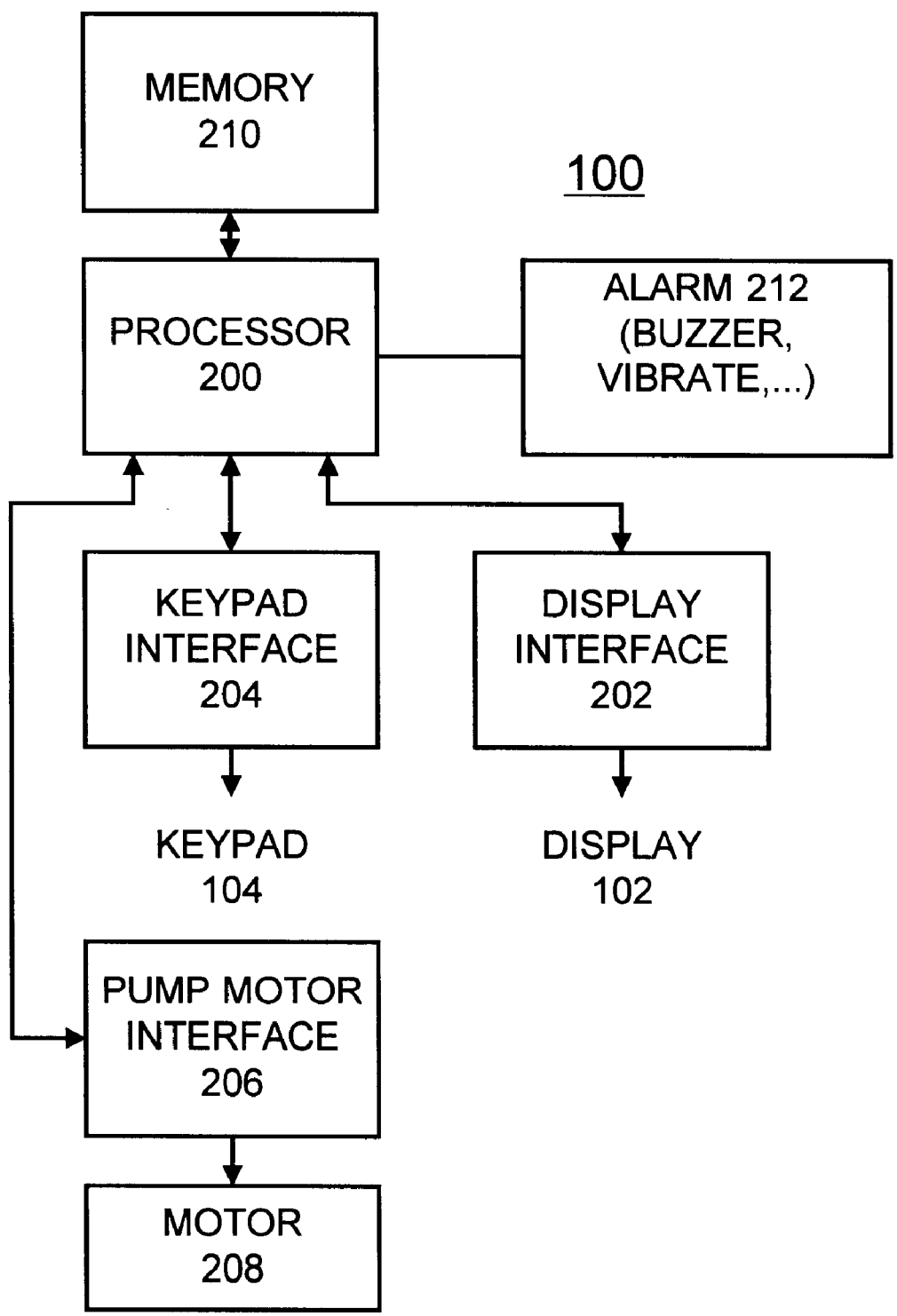
FIG. 2 is a block diagram representation illustrating an insulin pump for implementing methods for providing a forgotten bolus warning for an insulin pump user in accordance with the preferred embodiment.

Referring to FIG. 2, there is shown a block diagram representation illustrating the insulin pump 100 for implementing methods for providing a forgotten bolus warning for an insulin pump user in accordance with the preferred embodiment. Insulin pump 100 includes a processor 200 connected to a display interface 202 coupled to the display 102 and a keypad interface 204 coupled to the keypad 104. Processor 200 is connected to a pump motor interface 206 connected to a motor 208 for delivering insulin doses. Processor 200 is connected to a memory 210 that provides program and data storage. Processor 200 is connected to an alarm 212, such as a buzzer, a vibrator or the like, providing an alarm function or forgotten bolus warning for an insulin pump user.

Processor 200 is suitably programmed to execute the flow charts of FIGS. 3, 4, 5, and 6 of the preferred embodiment. Insulin pump 100 may be implemented using any suitable insulin pump, such as various commercially available insulin pumps.

In accordance with feature of the preferred embodiment, insulin pump 100 includes a reminder feature or forgotten bolus warning for an insulin pump user. The user has the capability of programming expected mealtimes by day of the week and a time duration or wait period starting at the expected eating time, after which a warning is produced, such as audible sounds or vibration, if a bolus is not administered. The user programs expected mealtimes that can be different on a daily basis or on a weekday and a weekend basis. The user is prompted for a time period to wait before a warning is issued if no bolus were administered after the expected mealtime has passed. For example, the user may program the expected mealtime of 7 a.m. on weekdays and for a warning to be issued 30 minutes past mealtime if no bolus were administered. Also each of the wait periods for issuing a warning can be set independently. Such independent wait periods can be advantageous because perhaps evening mealtimes might not be quite as predictable as breakfast or lunch mealtimes.

Referring to FIGS. 3, 4, 5, and 6 there are shown flow charts illustrating exemplary sequential steps for providing a forgotten bolus warning for an insulin pump user in accordance with the preferred embodiment.

Figure 3:
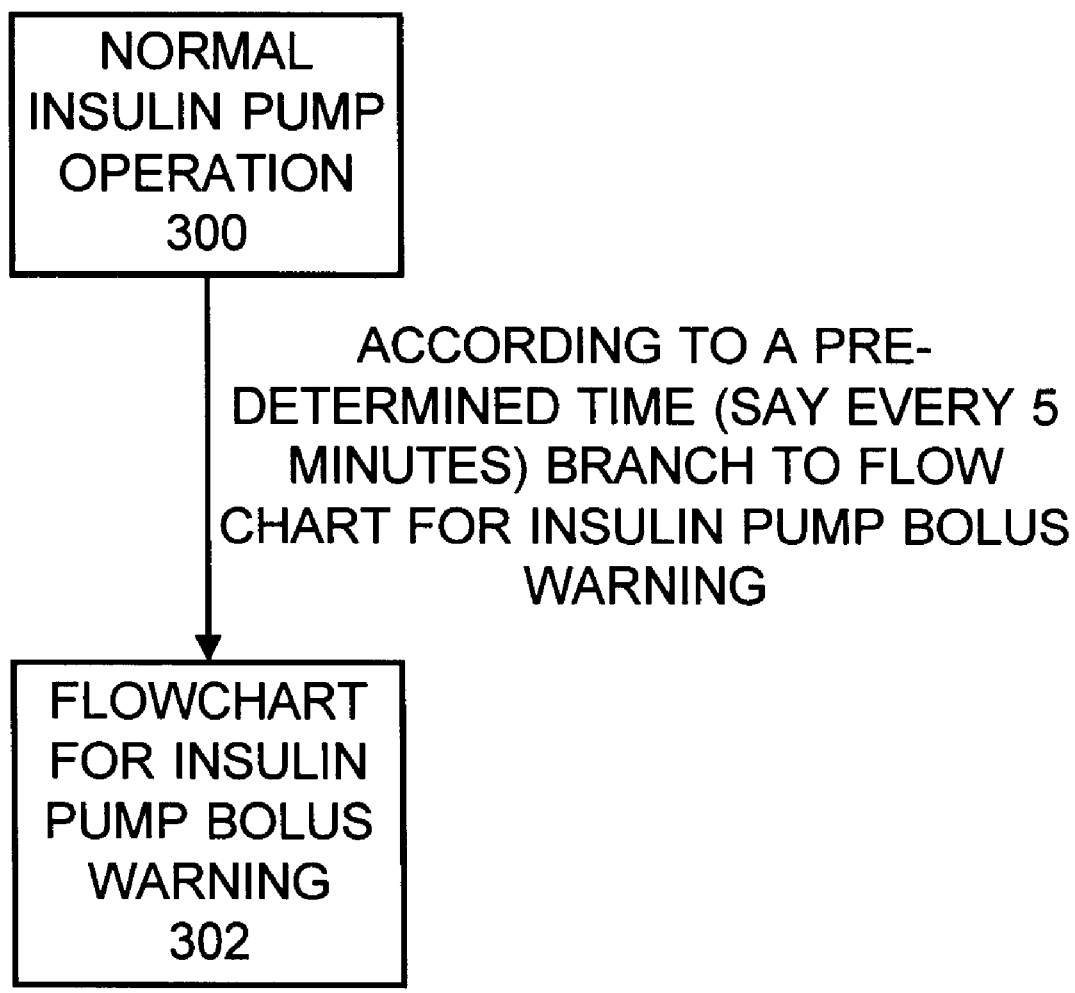
FIGS. 3, 4, 5, and 6 are flow charts illustrating exemplary sequential steps for providing a forgotten bolus warning for an insulin pump user in accordance with the preferred embodiment.

In FIG. 3, there are shown exemplary sequential steps for main insulin pump operation. Normal insulin pump operation is performed as indicated in a block 300. According to a predetermined time, for example every 5 minutes, the insulin pump operation branches to a flowchart for insulin pump bolus warning as indicated in a block 302. A flowchart of exemplary sequential steps for providing an insulin pump bolus warning is illustrated and described with respect to FIG. 6.

Figure 4:
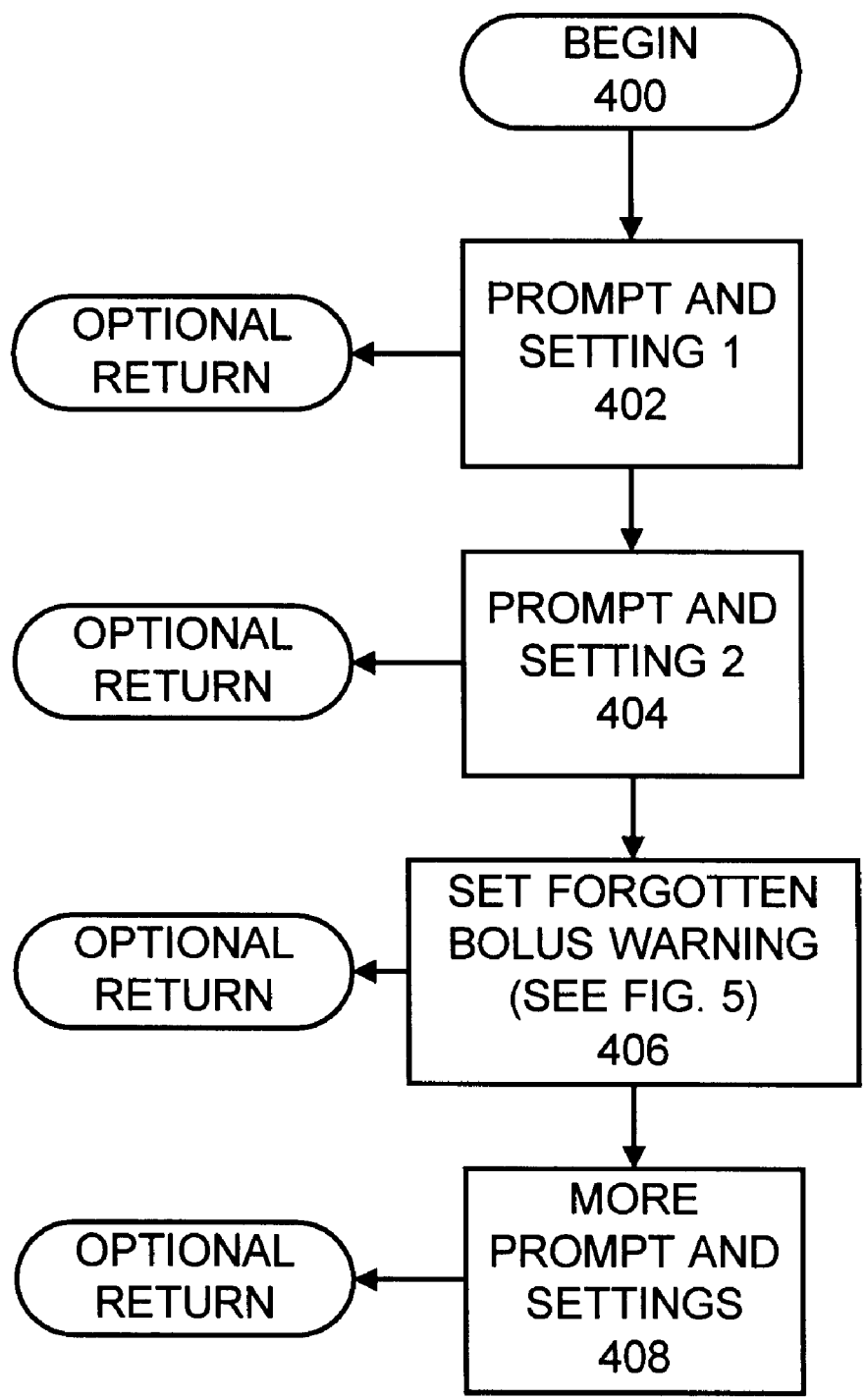
Figure 5:
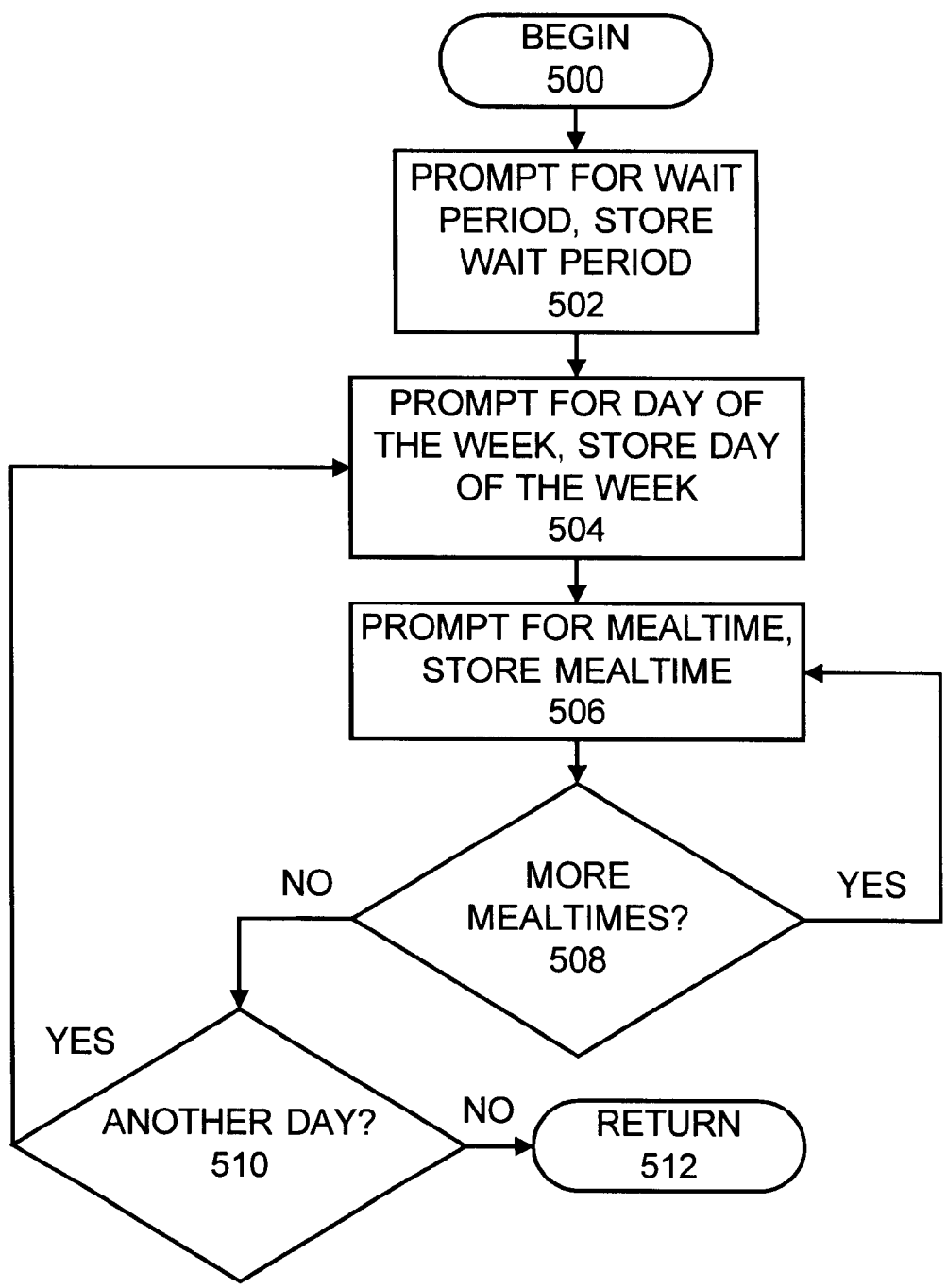

In FIG. 4, there are shown exemplary steps for insulin pump bolus warning setting starting at a block 400. As indicated in a block 402, the user is prompted for entering a first setting 1. As indicated in a block 404, the user is prompted for entering a second setting 2. The user is prompted to set forgotten bolus warning as indicated in a block 406 which sets a bolus warning flag. FIG. 5 illustrates the detailed steps to set forgotten bolus warning at block 406. As indicated in a block 408, the user is prompted for entering more settings. At each of the blocks 402, 404, 406 and 408, sequential operations optionally return. In FIG. 4, sequential steps are shown at blocks 402, 404, 406 and 408. It should be understood that a parallel menu format could be used instead of the sequential steps.

Referring now to FIG. 5, there are shown exemplary steps for setting insulin pump forgotten bolus warning starting at a block 500. The user is prompted for a wait period and the user entered wait period is stored as indicated in a block 502. The user is prompted for a day of the week and the day of the week is stored as indicated in a block 504. Next the user is prompted for a mealtime and the user entered mealtime is stored as indicated in a block 506. Additionally, a warning wait period can be stored with each mealtime stored at block 506. Checking for another mealtime is performed as indicated in a decision block 508. When another mealtime is found, the sequential operations return to block 506 where the user is prompted for a mealtime and the user entered mealtime is stored. When another mealtime is not found, then checking for another day of the week is performed as indicated in a decision block 510. When another day of the week is found, the sequential operations return to block 504 where the user is prompted for a day of the week and the day of the week is stored. Otherwise, the sequential operations return as indicated in a block 512.

It should be understood that a default wait period or periods and default mealtimes for different days of the week are provided. It should be understood that the wait period could be stored for each meal.

Figure 6:
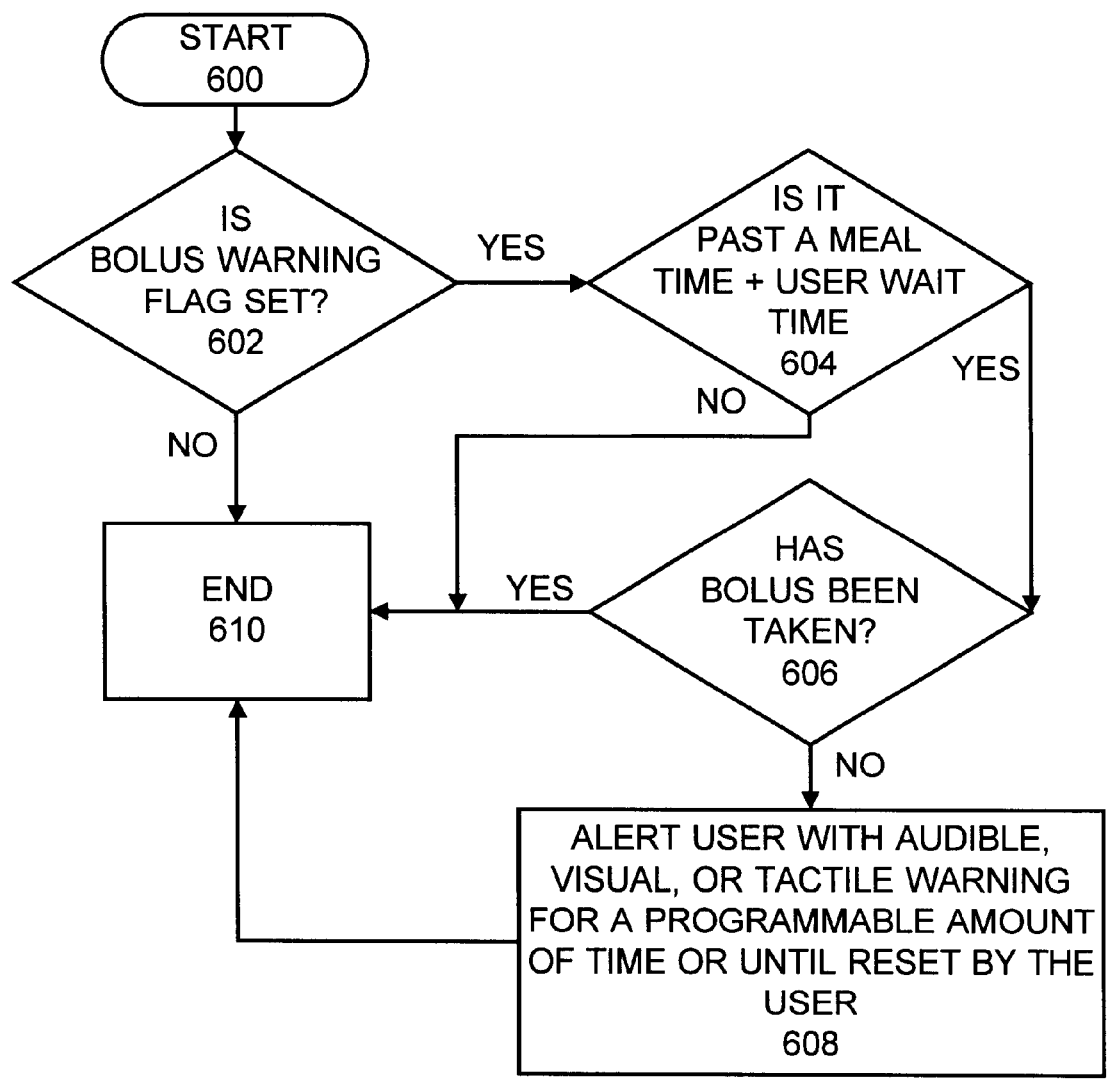

Referring now to FIG. 6, there are shown exemplary steps for generating the insulin pump forgotten bolus warning starting at a block 600. Checking whether the bolus warning flag is set is performed as indicated in a decision block 602. When the bolus warning flag is set, then checking whether it is past a mealtime plus the user set wait time is performed as indicated in a decision block 604. When the bolus warning flag is set, then the sequential steps end as indicated in a block 610. When it is past a mealtime plus the user set wait time, then checking whether the bolus has been taken is performed as indicated in a decision block 606. When it is not past a mealtime plus the user set wait time, then the sequential steps end at block 610. When the bolus has not been taken, then the user is alerted with an audible, visual, or tactile warning for a programmable amount of time as indicated in a block 608. The audible, visual, or tactile warning at block 608 can be continue until reset by the user. When the bolus has been taken, then the sequential steps end at block 610.

Referring now to FIG. 7, an article of manufacture or a computer program product 700 of the invention is illustrated. The computer program product 700 includes a recording medium 702, such as, a non-volatile semiconductor storage device, a floppy disk, a high capacity read only memory in the form of an optically read compact disk or CD-ROM, a tape, a transmission type media such as a digital or analog communications link, or a similar computer program product. Recording medium 702 stores program means 704, 706, 708, 710 on the medium 702 for carrying out the methods for providing a forgotten bolus warning for an insulin pump user in accordance with the preferred embodiment in the insulin pump 100 of FIG.

A sequence of program instructions or a logical assembly of one or more interrelated modules defined by the recorded program means 704, 706, 708, 710, direct the insulin pump 100 for providing a forgotten bolus warning for an insulin pump user in accordance with the preferred embodiment.

While the present invention has been described with reference to the details of the embodiments of the invention shown in the drawing, these details are not intended to limit the scope of the invention as claimed in the appended claims.

What is claimed is:

1. A method for providing a forgotten bolus warning for an insulin pump user, an insulin pump for performing the method comprising the steps of:

receiving and storing by the insulin pump user selections for mealtimes;

receiving and storing by the insulin pump a user selection for a warning wait period;

identifying by the insulin pump a time past a mealtime plus said user selection for said warning wait period;

responsive to said identified time, checking by the insulin pump for a bolus having been taken; and responsive to detecting by the insulin pump no bolus having been taken, alerting the user with the forgotten bolus warning.

2. A method for providing a forgotten bolus warning for an insulin pump user as recited in claim 1 wherein the step of receiving and storing by the insulin pump user selections for mealtimes includes the steps of prompting for a day of the week and storing a day of the week; responsive to said stored day of the week, prompting for a mealtime and storing a mealtime; checking for a next mealtime; and responsive to an identified next mealtime, prompting for a mealtime and storing a mealtime.

3. A method for providing a forgotten bolus warning for an insulin pump user as recited in claim 2 includes the steps of sequentially repeating the steps of prompting for a day of the week and storing a day of the week; responsive to said stored day of the week, prompting for a mealtime and storing a mealtime; checking for a next mealtime; and responsive to an identified next mealtime, prompting for a mealtime and storing a mealtime for each day of the week.

4. A method for providing a forgotten bolus warning for an insulin pump user as recited in claim 2 wherein the step of receiving and storing by the insulin pump a user selection for a warning wait period includes the step of storing a user selection for said warning wait period with each stored mealtime.

5. A method for providing a forgotten bolus warning for an insulin pump user as recited in claim 1 wherein the step responsive to detecting by the insulin pump no bolus having been taken, of alerting the user with the forgotten bolus warning includes the step of alerting the user with an audible forgotten bolus warning for a programmable period of time.

6. A method for providing a forgotten bolus warning for an insulin pump user as recited in claim 1 wherein the step responsive to detecting by the insulin pump no bolus having been taken, of alerting the user with the forgotten bolus warning includes the step of alerting the user with a visual forgotten bolus warning for a programmable period of time.

7. A method for providing a forgotten bolus warning for an insulin pump user as recited in claim 1 wherein the step responsive to detecting by the insulin pump no bolus having been taken, of alerting the user with the forgotten bolus warning includes the step of alerting the user with a tactile forgotten bolus warning for a programmable period of time.

8. A method for providing a forgotten bolus warning for an insulin pump user as recited in claim 1 wherein the step responsive to detecting by the insulin pump no bolus having been taken, of alerting the user with the forgotten bolus warning includes the step of providing an audible, visual, or tactile warning until reset by the user.

9. An insulin pump for providing a forgotten bolus warning for an insulin pump user, said insulin pump comprising:
   an insulin pump processor;
   a display coupled to said insulin pump processor for prompting the user for user selections;
   a keypad coupled to said insulin pump processor for receiving and storing user selections for mealtimes and for a warning wait period;
   said insulin pump processor for identifying a time past a mealtime plus said user selection for said warning wait period and for checking for a bolus having been taken; and
   said insulin pump processor responsive to detecting no bolus having been taken, for alerting the user with the forgotten bolus warning.

10. An insulin pump for providing a forgotten bolus warning for an insulin pump user as recited in claim 9 includes an alarm coupled to said insulin pump processor; said alarm for providing the forgotten bolus warning.

11. An insulin pump for providing a forgotten bolus warning for an insulin pump user as recited in claim 10 wherein said alarm alerts the user with an audible, visual or tactile warning for a programmable amount of time.

12. An insulin pump for providing a forgotten bolus warning for an insulin pump user as recited in claim 10 wherein said alarm alerts the user with an audible, visual or tactile warning until reset by the user.

13. A computer program product providing a forgotten bolus warning for a user of an insulin pump including an insulin pump processor unit, said computer program product including a plurality of computer executable instructions stored on a computer readable medium, wherein said instructions, when executed by said processor unit, cause the insulin pump processor unit to perform the steps of:
   receiving and storing by the insulin pump processor unit user selections for mealtimes and for a warning wait period;
   identifying by the insulin pump processor unit a time past a mealtime plus said user selection for said warning wait period;
   responsive to said identified time, checking by the insulin pump processor unit for a bolus having been taken; and
   responsive to detecting by the insulin pump processor unit no bolus having been taken, alerting the user with the forgotten bolus warning.

14. A computer program product providing a forgotten bolus warning for a user of an insulin pump as recited in claim 13 wherein said instructions, when executed by said processor unit, cause the insulin pump processor unit to perform the steps of: prompting the user for entering said user selections for mealtimes and for a warning wait period.

15. A computer program product providing a forgotten bolus warning for a user of an insulin pump as recited in claim 13 wherein the step of alerting the user with the forgotten bolus warning includes the step of providing an audible, visual, or tactile warning until reset by the user.

16. A computer program product providing a forgotten bolus warning for a user of an insulin pump as recited in claim 13 wherein the step of alerting the user with the forgotten bolus warning includes the step of providing an audible, visual, or tactile warning for a programmable period of time.

* * * * *